United States Patent [19]

Prevedello et al.

[11] 4,028,395

[45] June 7, 1977

[54] METHOD FOR THE PREPARATION OF OCTENE-NITRILE ORGANIC COMPOUNDS AND COMPOUNDS OBTAINED THEREBY

[75] Inventors: Aldo Prevedello; Edoardo Platone, both of San Donato Milanese (Milan), Italy

[73] Assignee: Snam Progetti, S.p.A., San Donato, Milanese, Italy

[22] Filed: Oct. 30, 1975

[21] Appl. No.: 627,349

[30] Foreign Application Priority Data

Oct. 30, 1974   Italy ................................. 28956/74

[52] U.S. Cl. ..................... 260/465.4; 260/465.5 R; 260/465.6; 260/465.7; 260/465.9; 252/522
[51] Int. Cl.² ............... C07C 121/30; C07C 121/34
[58] Field of Search ................................ 260/465.4

[56] References Cited

UNITED STATES PATENTS

| | | | |
|---|---|---|---|
| 3,168,550 | 2/1965 | Blumenthal | 260/465.4 X |
| 3,354,196 | 11/1967 | Julia | 260/465.4 X |
| 3,655,722 | 4/1972 | Mitchell et al. | 260/465.9 |
| 3,746,749 | 7/1973 | Mitsuyasu et al. | 260/465.4 X |

OTHER PUBLICATIONS

Szmant, Organic Chemistry, 1957, p. 242.
Zhurnal Obshikei–Khimii, vol. 29, Apr.–June 1959, p. 1189.

*Primary Examiner*—Joseph Paul Brust
*Attorney, Agent, or Firm*—Ralph M. Watson

[57] ABSTRACT

A method for the preparation of a certain class of octenenitriles is disclosed, which uses as the starting compound the 3,7-dimethyl-3-hydroxy-6-octenenitrile: the reaction is a simple dehydration reaction or, in certain cases, an esterification or etherification. The method as disclosed is very simple and cheap and the product thus obtained can be used in the perfume and cosmetic industry.

1 Claim, No Drawings

METHOD FOR THE PREPARATION OF OCTENE-NITRILE ORGANIC COMPOUNDS AND COMPOUNDS OBTAINED THEREBY

This invention relates to the preparations of octenenitrile compounds and the compounds obtained thereby. The compounds which can be obtained with the method of the present invention have the following structural formula:

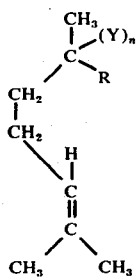

wherein Y is a halogen atom, a hydrocarbon radical, an ether, an ester, an amine, a phoshine and the like, whereas $n$ can be equal to zero or one and R is —CH$_2$—CN if $n$ is 1 and is =CH—CN if $n$ is 0. More particularly, the present invention is related to the organic compounds aforementioned with $n = 1$.

The importance of the ocetene-nitrile compounds is known, since they are more and more widely employed for the production of perfumed essences to be used for the preparation of perfumes, and in the soap, detergent and cosmetic industry as well.

Heretofore these compounds, and especially the compounds having the above reported structural formula in which $n$ is zero, were obtained through chemical procedures which were cumbersome and, inter alia, included a large number of chemical reactions: the yields were low and the selectively poor while, on other occasions, admixtures of these products were obtained, such as in the case of the reaction of methylheptenone with cyanacetic acid which was conductive to a mixture of octadienenitriles, from which, geranonitrile and neronitrile, that is, the most interesting compounds to the end of perfume production, had subsequently to be separated with particularly laborious distillation runs. It has now been found that the synthesis of these octenenitrile compounds can be achieved in a manner which is both convenient and cheap, by using as the starting compound the 3,7-dimethyl-3-hydroxy-6-octenenitrile which is the subject-matter of copending patent application Ser. No. 627,350 by the same applicants hereof.

The use of such a compound in the synthesis of the above compounds has permitted surprisingly to widen the possibility of obtaining these compounds with a high selectivity, through reactions which are known to those skilled in the art, until obtaining the expected compound.

More detailedly, this interesting compound can be used as the starting product for the preparation of the alphabeta unsaturated octadienenitriles, which are known, as outlined above, under the names of geranonitrile and neronitrile. The formation of such compounds takes place directly, through a simple dehydration reaction. An important feature of this reaction is that it is principally conducive to the formation of the trans isomer (geranonitrile) and the cisisomer (neronitrile) with good yields and selectively. Thus, products having a double bond conjugated relative to the CN group are obtained with quantitative yields. In addition to this dehydration reaction, the intermediate compound considered herein can be used for the preparation of products which are also within the scope of this invention, in which $n$ is 1, through known reactions, such as esterification and etherifications.

More particularly, an acetylation reaction can be carried out, which consists in reacting the compound concerned with acetyl chloride. The reaction temperature is maintained between 20° C and 100° C in the presence of bases, more specifically tertiary bases, and, after an appropriate fractioning in order to separate the acetyl derivative from the 3,7-dimethyl-3-hydroxy-6-octenenitrile when did not react, a compound is obtained which has high stability properties and is deeply scented, so that it can be used for stabilizing perfume mixtures.

The following examples, which are for illustration only, and are nonlimiting, show the methods for obtaining the compounds the subject of the present invention.

EXAMPLE 1

This example illustrates the dehydration reaction of 3,7-dimethyl-3-hydroxy-6-octenenitrile.

One gram (1 gr.) of 3,7-dimethyl-3-hydroxy-6-octenenitrile are heated during one hour and 30 mins to the temperature of 210° C–230° C in the presence of 1.5 grs. of basic alumina. Upon cooling, the reaction mixture is washed with ethyl ether, whereafter the solvent is stripped. A liquid is obtained, which has a pleasant smell and which, upon a chromatography as performed in a 20% LAC 728 column on chromosorb P, has proven to be mainly composed by two compounds: these latter exhibited, on mass spectrography, a mol. wt 149 for both. The NMR test, as performed on the mixture aforesaid did not show any peak which could be attributed to protons of the —CH$_2$—CN type so that any elimination product other than an unsaturated alpha-beta nitrile can be excluded. IR analysis shows that a conjugated nitrile, — is in the question, since the CN stretching falls to 2,216 cm$^{116}$ [1]. It can thus be concluded that there have been formed, with virtually quantitative yields, the cis and trans isomers of 3,7-dimethyl-2,6-octadienenitrile.

EXAMPLE 2

In the present example there is illustrated the acetylation reaction of 3,7-dimethyl-3-hydroxy-6-octenenitrile.

A 100-ml flaks, immersed in a thermostatic bath and equipped with a dropping funnel and bubbled condenser is charged with 8.45 grs. (0.05 mol) of hydroxynitrile. There are added, then, 6.66 grs. (0.055 mol) of N,N-dimethyl aniline, whereafter the reaction mixture is brought to a temperature of 75° C approx.

Through the dropping funnel there are then added, during 2hours approximately, 3.93 grs. (0.05 mol) of acetyl chloride. The addition is made in small increments, the temperature of the thermostatic bath being still maintained at about 75° C. On completion of the addition, the mixture is maintained at such temperature during two additional hours. The reaction mixture is allowed to cool and there are added about 20 mls water and then 20 mls of ethyl ether. The ethereal layer is separated and then extracted twice with a 20% solution of sulphuric acid and then with a saturated solution of sodium bicarbonate and finally with water until a neutral reaction is achieved. The ethereal solution is dried overnight over anhydrous sodium sulphate. Upon the stripping of ether, there are obtained 10 grs. of a mixture which contains about the 95% of the acetyl derivative and 5% of 3,7-dimethyl-3-hydroxy-6-octenenitrile. The reaction mixture can be purified by an appropriate fractionation. (The product distils at a temperature of T=108.5° C and under a pressure P = 2 mms. of mercury.) This product has been identified by the data which can be obtained from NMR, IR and mass spectroscopy. The principal spectroscopical properties of the compound are:

NMR (solvent $CCl_4$; internal standard HMDS)

| Proton type | Chemical shift (ppm) |
|---|---|
| $>C=CH$ | 5.0 (m) |
| $-CH_2-CN$ | 2.9 (q) |
| $CH_3$ $\mid$ $-C-$ $\mid$ | 1.5 (s) |
| $-CH_2-CH_2-$ | 1.6 – 2.0 (m) |
| $CH_3$ $>C=C<$ $CH_3$ | 1.6 (d) |

| Proton type | Chemical shift (ppm) |
|---|---|
| $CH_3-COO-$ | 2.0 (s) |

The infrared spectrum confirms the presence of the following functional groups:

| IR : | C = O | stretching | 1737 cm$^{-1}$ |
|---|---|---|---|
| | C N | " | 2248 cm$^{-1}$ |

What is claimed is:
1. Octenenitrile organic compounds having the structural formula:

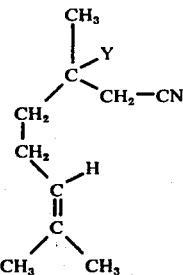

wherein Y is a radical having the formula —O—CO—CH$_3$.

* * * * *